(12) United States Patent
Creedon et al.

(10) Patent No.: US 10,949,969 B1
(45) Date of Patent: Mar. 16, 2021

(54) PUPIL EDGE REGION REMOVAL IN DIGITAL IMAGING

(71) Applicant: Welch Allyn, Inc., Skaneateles Falls, NY (US)

(72) Inventors: William Niall Creedon, Portland, OR (US); Eric Joseph Laurin, Beaverton, OR (US); Richard Allen Mowrey, Ottawa (CA)

(73) Assignee: Welch Allyn, Inc., Skaneateles Falls, NY (US)

( * ) Notice: Subject to any disclaimer, the term of this patent is extended or adjusted under 35 U.S.C. 154(b) by 101 days.

(21) Appl. No.: 16/357,992

(22) Filed: Mar. 19, 2019

Related U.S. Application Data

(60) Provisional application No. 62/645,375, filed on Mar. 20, 2018.

(51) Int. Cl.
| | |
|---|---|
| G06T 7/00 | (2017.01) |
| G06T 3/40 | (2006.01) |
| G06T 7/12 | (2017.01) |
| A61B 3/12 | (2006.01) |
| A61B 3/00 | (2006.01) |
| G06T 7/136 | (2017.01) |

(52) U.S. Cl.
CPC .......... G06T 7/0012 (2013.01); A61B 3/0008 (2013.01); A61B 3/12 (2013.01); G06T 3/4007 (2013.01); G06T 7/12 (2017.01); G06T 7/136 (2017.01); *G06T 2207/30041* (2013.01)

(58) Field of Classification Search
CPC ....... A61B 3/112; A61B 5/6821; G06F 3/013; G06T 7/12; G06T 7/13
See application file for complete search history.

(56) References Cited

U.S. PATENT DOCUMENTS

| | | | | |
|---|---|---|---|---|
| 5,831,736 A * | 11/1998 | Lichtman | ............... | G01B 11/24 356/613 |
| 6,036,316 A * | 3/2000 | Arita | ...................... | A61B 3/113 351/205 |
| 6,325,765 B1 * | 12/2001 | Hay | ........................ | A61B 3/103 600/558 |
| 6,419,638 B1 * | 7/2002 | Hay | ...................... | A61B 3/0025 600/558 |
| 8,345,922 B2 * | 1/2013 | Inada | .................... | G06K 9/0061 382/103 |
| 9,237,846 B2 | 1/2016 | Mowrey et al. | | |
| 9,402,538 B2 | 8/2016 | Mowrey et al. | | |
| 10,417,495 B1 * | 9/2019 | Davami | .................... | G06T 7/75 |
| 2006/0008116 A1 * | 1/2006 | Kiraly | ........................ | G06T 7/20 382/103 |
| 2010/0284576 A1 * | 11/2010 | Tosa | ...................... | G06K 9/0061 382/117 |

(Continued)

OTHER PUBLICATIONS

U.S. Appl. No. 15/926,121, filed Mar. 20, 2018.

*Primary Examiner* — Dung Hong
(74) *Attorney, Agent, or Firm* — Merchant & Gould P.C.

(57) ABSTRACT

A digital imaging system processes digital images of a subject's fundus and/or pupils to determine pupil edge region pixels. Pupil edge region pixels are removed and a glint area is identified and interpolated over. Resulting images can be processed to determine a pixel intensity distribution slope. Using the pixel intensity distribution slope, refractive error determinations can be made.

16 Claims, 10 Drawing Sheets

(56) References Cited

U.S. PATENT DOCUMENTS

| | | | |
|---|---|---|---|
| 2011/0228975 A1* | 9/2011 | Hennessey | G06K 9/00624 |
| | | | 382/103 |
| 2012/0069195 A1* | 3/2012 | Chang | H04N 5/3572 |
| | | | 348/182 |
| 2012/0212598 A1* | 8/2012 | Mowrey | A61B 5/0013 |
| | | | 348/78 |
| 2012/0293773 A1* | 11/2012 | Publicover | A61B 3/113 |
| | | | 351/210 |
| 2015/0220157 A1* | 8/2015 | Marggraff | G06F 1/1694 |
| | | | 345/156 |
| 2016/0286092 A1* | 9/2016 | Ohta | H04N 1/624 |
| 2017/0046851 A1* | 2/2017 | Lin | G06T 7/12 |
| 2017/0091520 A1* | 3/2017 | Ishii | G06K 9/00617 |
| 2018/0089834 A1* | 3/2018 | Spizhevoy | G06K 9/627 |
| 2019/0187482 A1* | 6/2019 | Lanman | G06F 3/011 |
| 2020/0029802 A1* | 1/2020 | Lane | A61B 3/02 |

\* cited by examiner

PUPIL EDGE REGION REMOVAL IN DIGITAL IMAGING

INTRODUCTION

Various types of abnormalities and diseases can be screened for by analyzing images captured by cameras. For example, photorefraction vision screening can evaluate whether a person has one or more types of refractive errors. In photorefractive vision screening, light from an external source enters the eye through the pupil and is focused to create a small illuminated spot on the retina. Some of the light from this retinal spot is returned out of the eye through the pupil after interaction with different layers of the retina. The pattern of light exiting the pupil is determined by the optics of the eye and is dominated by an examinee's refractive error (focusing errors of the eye).

Trained medical professionals use cameras during eye examinations for disease screening. The cameras can produce images of the back of the eye and trained medical professionals use those images to diagnose and treat one or more diseases. These images are produced either with pharmacological pupil dilation, known as mydriatic fundus imaging, or without pharmacological pupil dilation, known as non-mydriatic fundus imaging. Because pupil dilation is inversely related, in part, to the amount of ambient light, non-mydriatic fundus imaging usually occurs in low lighting environments.

SUMMARY

Embodiments of the disclosure are directed to pupil area processing in digital imaging. Generally, systems and methods disclosed herein process digital images and identify pupil edges in the digital images. Typically, a pupil threshold value is determined and used to remove pupil edge region pixels from digital images.

In one aspect, a method for removing a pupil edge region from a digital image is disclosed. The method includes identifying a plurality of pupil pixels in the digital image; identifying a glint area in the plurality of pupil pixels; generating interpolated pupil data, including interpolating a first portion of the plurality of pupil pixels, the first portion including the glint area; determining a representative intensity of the interpolated pupil data; using the representative intensity, generating a threshold; generating a binary image of the digital image using the threshold; removing a pupil area of the binary image; averaging remaining outer pupil pixel intensity values in the binary image, thereby generating a pupil edge region threshold; and removing the pupil edge region from the digital image using the pupil edge region threshold.

In another aspect, method for generating a mask of a pupil edge region in a digital image is disclosed. The method includes receiving the digital image; identifying a plurality of pupil pixels in the digital image; identifying a glint area in the plurality of pupil pixels; generating interpolated pupil data, including interpolating a first portion of the plurality of pupil pixels, the first portion including the glint area; determining a representative intensity of the interpolated pupil data; using the representative intensity, generating a threshold; generating a binary image of the digital image using the threshold; removing a center pupil area of the binary image; averaging remaining outer pupil pixel intensity values in the binary image, thereby generating a pupil edge region threshold; and using the pupil edge region threshold, applying a mask to the digital image.

In another aspect, a medical imaging system includes an illumination assembly, a digital camera assembly, a processing unit, and memory. The memory stores instructions that, when executed by the processing unit, cause the medical imaging system to: illuminate an eye fundus of a subject with the illumination assembly; receive a digital image with the digital camera assembly; identify a plurality of pupil pixels in the digital image; identify a glint area in the plurality of pupil pixels; generate interpolated pupil data, including interpolating a first portion of the plurality of pupil pixels, the first portion including the glint area; determine a representative intensity of the interpolated pupil data; use the representative intensity to generate a threshold; generate a binary image of the digital image using the threshold; remove a center pupil area of the binary image; average remaining outer pupil pixel intensity values in the binary image, thereby generating a pupil edge region threshold; and remove a pupil edge region from the digital image using the pupil edge region threshold, including removing pixels having an intensity value that is lower than the pupil edge region threshold.

The details of one or more embodiments are set forth in the accompanying drawings and the description below. Other features, objects, and advantages of these embodiments will be apparent from the description, drawings, and claims.

DESCRIPTION OF THE FIGURES

The following drawing figures, which form a part of this application, are illustrative of described technology and are not meant to limit the scope of the disclosure in any manner.

DETAILED DESCRIPTION

Figure 1:
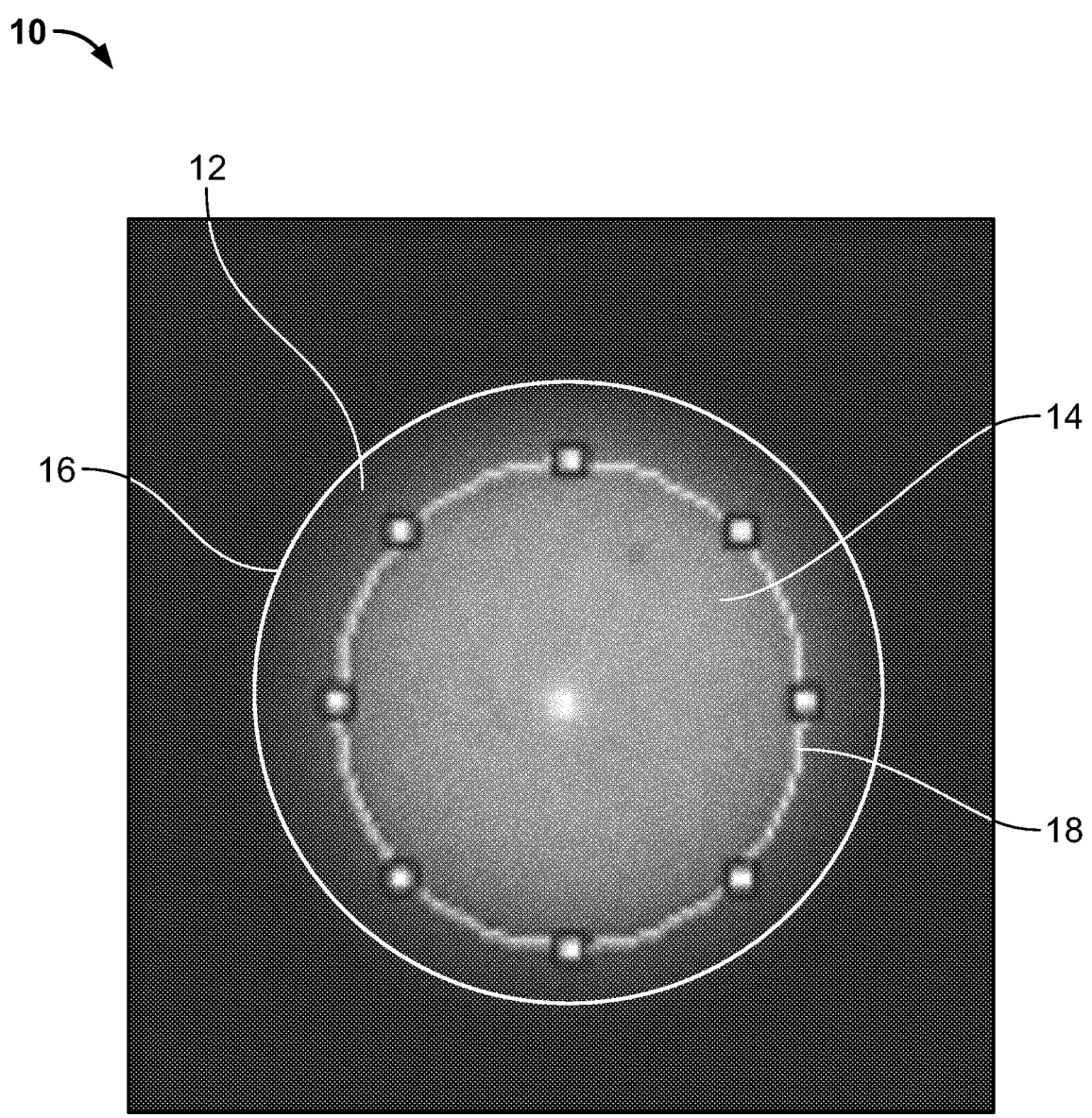
FIG. 1 is an example digital pupil image showing an embodiment of a pupil edge region.

Various embodiments of the present disclosure will be described in detail with reference to the drawings, wherein like reference numerals represent like parts and assemblies throughout the several views. Additionally, any examples set forth in this specification are not intended to be limiting and merely set forth some of the many possible embodiments.

Broadly, the present disclosure is directed to medical digital imaging. Certain types of medical digital imaging identify and/or analyze a subject's pupil. Systems and methods of this disclosure are directed towards pupil identification and analysis during medical digital imaging. In particular, systems and methods disclosed herein involve removing a pupil edge region in a digital image. Removing pupil edge regions finds application in, for example, photorefraction ocular screening.

Photorefraction ocular screening devices can determine refractive error by determining a slope of an intensity distribution of pixels across a pupil. The slope of the intensity distribution can be used to infer spherical error of a test subject's eye. Example determinations of a slope of the pixel intensity distribution across a pupil is shown in U.S. Pat. No. 9,237,846, titled "Photorefraction ocular screening device and methods," hereby incorporated by reference in its entirety, with particular reference to FIG. 15 and corresponding discussion.

Slope determination typically relies on an accurate detection of the pupil edge. Accurate determination of a pupil size is needed to infer a subject's spherical error from a calculated slope of a pixel intensity distribution. Generally, intensity distributions near the pupil edges decrease gradually. Accordingly, excluding pixels at, and adjacent to, the pupil edges when calculating a slope profile of the intensity distribution across the pupil can yield more accurate results. Such pixels are termed the "pupil edge region". That is, a "pupil edge region," as used herein, is an area including, and adjacent to, the outermost pupil pixels.

For explanation purposes, FIG. 1 shows an example digital pupil image 10 with pupil edge region 12 identified. As described in greater detail below, pupil edge region 12 can be determined by generating a pupil threshold value. Pupil edge region 12 includes pixels having an intensity value below the pupil threshold value. These pixels include pixels at the pixel edge 16. Pixels having intensity values equal to or greater than the pupil threshold value are in pixel region 14. Generally, ring 18 represents the pupil threshold value, generation of which is described in greater detail below.

Pupil size can be increased during examination through the use of mydriatic pharmaceuticals. For example, pupil sizes for subjects receiving mydriatic pharmaceuticals can be about 9 mm. However, pupil sizes can be much smaller in patients who have not taken mydriatic pharmaceuticals. Further, some members of the population have limited pupil diameters, such as people over the age of 65. It is not uncommon for people over the age of 65 to have pupil sizes smaller than 5 mm during non-mydriatic examination.

As pupil size decreases determining a slope of the intensity distribution accurately becomes more challenging. Particularly with pupil sizes less than 5 mm, digital images of such pupils have limited number of available pixels within the subject's pupil. Because there are fewer pupil pixels, the subject's glint occupies a large portion of pixels within the subject's pupil image. Generally, glint pixels are concentrated regions that have much brighter intensities than the surrounding pupil pixels. Thus, including glint pixels in intensity distribution determinations can cause inaccurate refractive error results. An example advantage of the systems and methods contemplated herein is improving the intensity distribution calculations by determining glint pixels and removing glint pixels from the intensity distribution calculations.

Additionally, the sampled region of the pupil extends near, or to, the pupil edge, where the intensity distributions decrease. Generally, pupil edge region pixels have lower intensities than pupil pixels. Thus, including edge pixels in intensity distribution determinations can cause inaccurate refractive error results. Another example advantage of the systems and methods contemplated herein is improving the intensity distribution calculations by determining pupil edge region pixels and removing pupil edge region pixels from the intensity distribution calculations.

Figure 2:
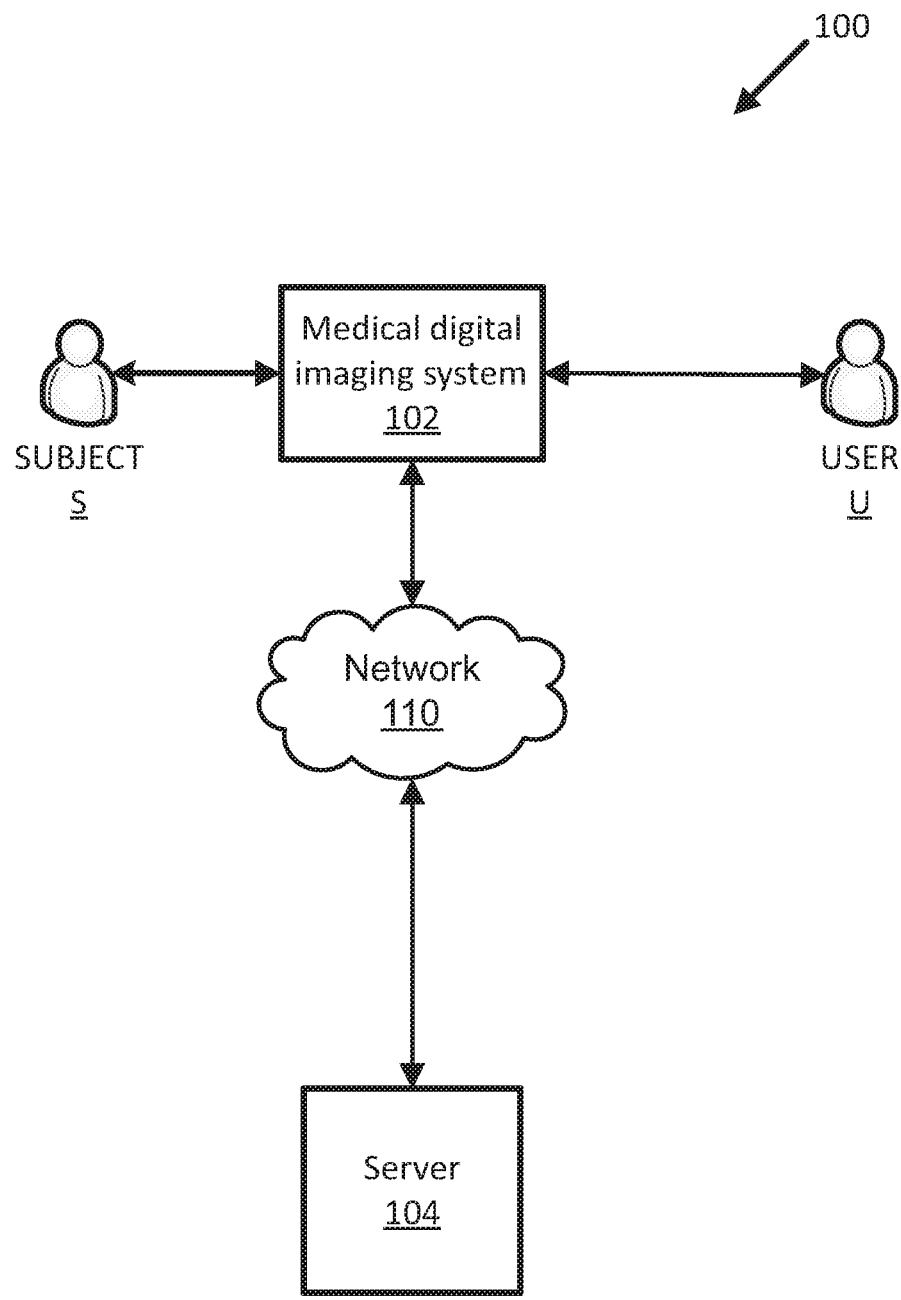
FIG. 2 is a schematic view of an example medical imaging environment.

FIG. 2 shows example medical imaging environment 100. Example medical imaging environment 100 includes medical digital imaging system 102, subject S, and user U. In some implementations, medical digital imaging system 102 is in communication with server 104, typically via network 110. User U uses medical digital imaging system 102 to obtain one or more images of subject S. User U can also use medical digital imaging system 102 to perform ocular eccentric photorefraction screening of subject S. Other embodiments can include more or fewer components.

In some implementations, medical imaging environment 100 is in a traditional medical environment, such as a general practice facility, an urgent care facility, a hospital, and the like. Alternatively, medical imaging environment 100 is a non-traditional medical environment, such as a school. In some instances, user U is not formally medically trained.

Medical digital imaging system 102 obtains and processes one or more digital images of an ocular fundus or pupil of subject S. Medical digital imaging system 102 can be used to assist user U when screening for, monitoring, or diagnosing various eye conditions or diseases. Example eye conditions and diseases include refractive error, hypertension, diabetic retinopathy, glaucoma and papilledema. It will be appreciated that user U operating medical digital imaging system 102 can be different from a person evaluating the resulting images. For example, medical digital imaging system 102 transmits one or more images or results to server 104. Then, a clinician different from user U can access server 104 to then analyze the results or images.

Medical digital imaging system 102 can have different sizes depending on the particular implementation. For example, medical digital imaging system 102 can be portable and sized such that it can be hand held. Portable, hand held sizing can be advantageous for off-site screening of a particular population, such as school children or nursing home occupants. In other implementations, medical digital imaging system 102 is configured for more stationary operations, such as within a medical facility.

In some implementations, medical digital imaging system 102 provides relatively immediate screening of subject S. Example screening can include capturing one or more images, displaying stimuli to subject S, capturing images of subject S's reaction to the stimuli, and an analysis of images including the subject's reaction. Based on this processing, medical digital imaging system 102 can display one or more different results reflecting analysis of the images.

Medical digital imaging system 102, in some implementations, displays stimuli and captures images of the subject's ocular fundus or pupils. In turn, medical digital imaging system 102 transmits those images for later viewing and analysis by trained clinicians or digital image processing algorithms.

Medical digital imaging system 102 is particularly configured to capture digital images including a pupil of subject S and to determine a pixel intensity distribution across the subject's pupil. These determinations can include the medical digital imaging system 102 identifying and removing pupil edge region pixels in the digital images. Other uses of determining pupil edge region pixels in digital image are contemplated.

One technique for fundus imaging requires mydriasis, dilation of a subject's pupil, which can be painful and/or inconvenient to the subject S. Example medical digital imaging system 102 can be used in mydriatic or non-mydriatic conditions. That is, medical digital imaging system 102 can capture images without requiring a mydriatic drug to be administered to the subject S before imaging.

In terms of pupil dilation, medical digital imaging system 102 can capture images with pupil sizes smaller than 5 mm. In some instances, medical digital imaging system 102 can capture wide FOV images with pupil sizes no greater than 4.5 mm, no greater than 3.5 mm or even no greater than 2.5 mm. Of course, medical digital imaging system 102 can capture images with larger pupil sizes, such as those greater than 5 mm.

Medical digital imaging system 102 includes a housing that supports system components. For instance, the housing supports one or two apertures for imaging one or two eyes at a time. In some embodiments, the housing supports positional guides for the subject S, such as an adjustable chin rest. The positional guides help align the subject's eyes with the apertures. In some embodiments, the apertures are adjustable to align them with the subject's eyes. Once the subject's eyes are aligned, user U can initiate image capture sequencing.

Medical digital imaging system 102 is typically connected to network 110. Network 110 can include any type of wireless network, a wired network, or any communication network known in the art. For example, wireless connections can include cellular network connections and connections made using protocols such as 802.11a, b, and/or g. In other examples, a wireless connection can be accomplished directly between medical digital imaging system 102 and an external display using one or more wired or wireless protocols, such as Bluetooth, Wi-Fi Direct, radio-frequency identification (RFID), or Zigbee. Other configurations are possible.

Server 104 communicates with medical digital imaging system 102 and additional devices. For example, server 104 receives images from medical digital imaging system 102 and stores the images, and possible accompanying data such as subject data, in one or more databases. Clinicians can then access stored images for analysis. Server 104 includes one or more components of computing device 801 shown in FIG. 12, described in more detail below.

Figure 3:
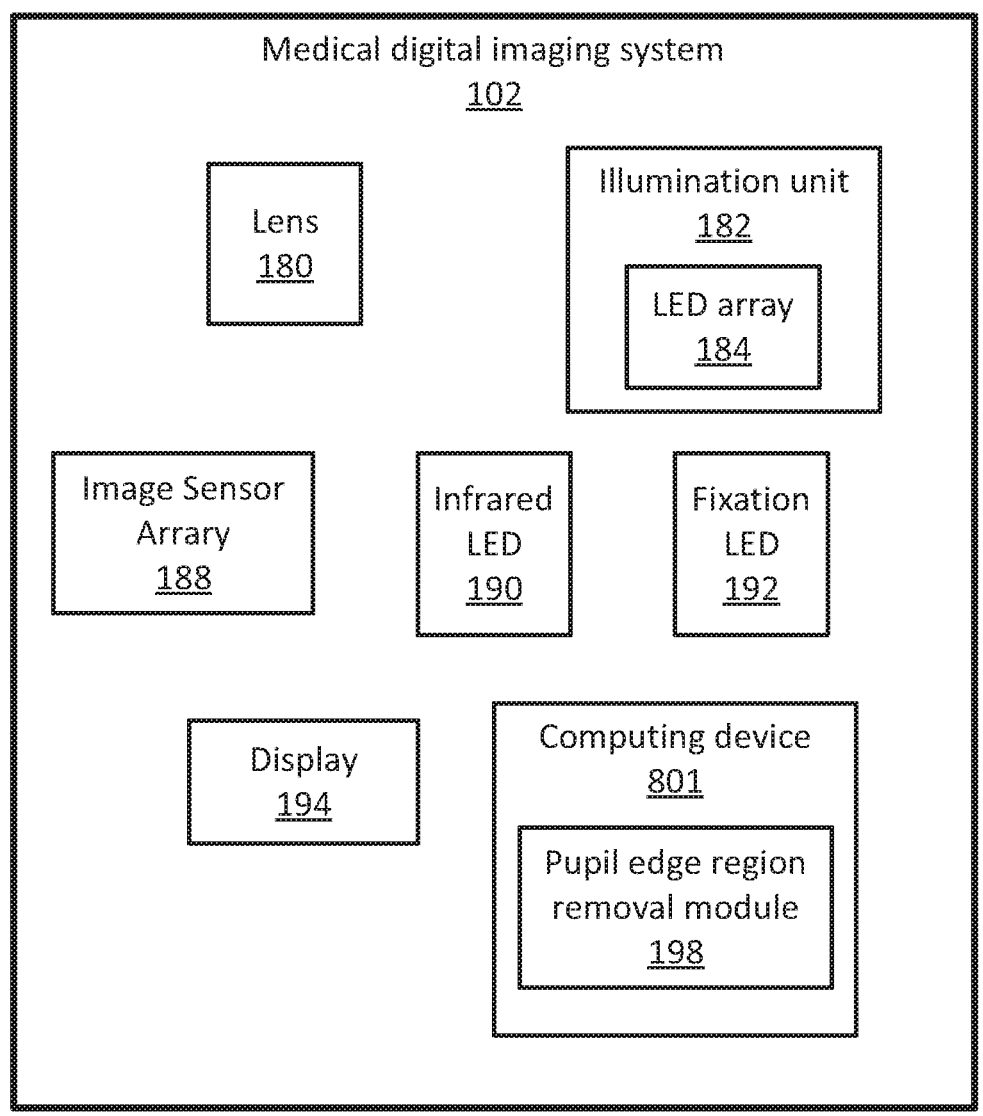
FIG. 3 is a schematic diagram showing example components of the medical digital imaging system used in the environment of FIG. 2.

FIG. 3 is a schematic diagram showing example components of medical digital imaging system 102. Medical digital imaging system 102 includes lens 180, illumination unit 182, image sensor array 188, infrared LED 190, fixation LED 192, and display 194. Each component is in communication with, at least, computing device 801. Additional components of medical digital imaging system 102, not shown in FIG. 3, can include a speaker unit, a range finder unit, and a front window. Commercial embodiments of medical digital imaging system 102 include the Welch Allyn RetinaVue™ 100 Imager and the Welch Allyn Spot™ Vision Screener (Welch Allyn, Skaneateles Falls, N.Y.). Other embodiments can include more or fewer components.

Lens 180 focuses light onto image sensor array 188. Typically, lens 180 is adjustable. For example, lens 180 can be implemented as a variable focus liquid lens or a mechanically adjustable lens. A liquid lens is an optical lens whose focal length can be controlled by the application of an external force, such as a voltage. The lens includes a transparent fluid, such as water or water and oil, sealed within a cell and a transparent membrane. By applying a force to the fluid, the curvature of the fluid changes, thereby changing the focal length. This effect is known as electrowetting. A mechanically adjustable lens can change a focal length of the lens using, for example, by a stepping motor, a voice coil actuator, an ultrasonic motor, or a piezoelectric actuator.

Illumination unit 182 is an optional component and illuminates the eye fundus during certain image capture operations. Illumination unit 182 is configured to illuminate the eye fundus of the subject. Illumination of illumination unit 182 is coordinated with operation of image sensor array 188.

As shown, illumination unit 182 includes LED array 184. In other embodiments, illumination unit 182 can include one or more additional lighting units. In addition, lighting elements in illumination unit 182 can include non-light-emitting diode components. LED array 184 can be single color or multi-color. For example, LED array 184 is a three-channel RGB LED, where each die is capable of independent and tandem operation.

Image sensor array 188 receives and processes light reflected off of the subject. Image sensor array 188 can be a complementary metal-oxide semiconductor (CMOS) sensor array or a charge coupled device (CCD) sensor. Image sensor array 188 has a plurality of rows of pixels and a plurality of columns of pixels. For example, in various implementations, the image sensor array has about 1280 by 1024 pixels, about 640 by 480 pixels, about 1500 by 1152 pixels, about 2048 by 1536 pixels, or about 2560 by 1920 pixels. Other pixel sizes are possible.

Pixels in image sensor array 188 include photodiodes that have a light-receiving surface and have substantially uniform length and width. During exposure, the photodiodes convert the incident light to a charge. Exposure and readout of image sensor array 188 can be performed as rolling shutter or global shutter.

In rolling shutter exposure and readout, each row of pixels is exposed for the same time duration, however, each row of pixels is exposed at different points in time. Rolling shutter exposure begins at a top row of image sensor array 188 and each row below is successively exposed and then readout. Typically, exposure of the row below begins before completing exposure and readout of the row above. In this way, at any given time during image sensor array 188 exposure, more than one row of pixels are exposed.

In global shutter exposure, all of the photodiodes in image sensor array 188 are exposed simultaneously and for the same length of time. Then readout is performed for each photodiode. Because all photodiodes are subjected to readout at the same time, usually the image sensor array must wait until readout is completed before beginning the next frame's exposure. Thus, global shutter operations typically have slower frame rates than rolling shutter operations.

Infrared LED 190 illuminates the eye fundus with near-infrared light. Infrared light emitted by infrared LED 190 preferably has a central wavelength of 850 nanometers. In some instances, infrared LED 190 emits infrared light during a preview and/or eye tracking mode. Alternatively, infrared LED 190 emits infrared light during image capture operations part of the ocular examination.

Medical digital imaging system 102 optionally includes fixation LED 192. Fixation LED 192 produces light to guide the subject's eye for alignment. Fixation LED 192 can be a single color or multicolor LED. For example, the fixation LED 192 can produce a beam of green light that appears as a green dot when subject S looks into the medical digital imaging system 102. Other colors and designs, such as a cross, "x" and circle are possible.

Medical digital imaging system 102 can also include display 194. Display 194 shows images and/or results produced by medical digital imaging system 102. In the example embodiment, a housing supports display 194. In other embodiments, display 194 connects to the image processor through wired or wireless connection, and can be instantiated as a smart phone, tablet computer, or external monitor.

Medical digital imaging system 102 also includes computing device 801, which typically includes a processing unit and a computer readable storage device. In some embodiments, the computer-readable storage device stores data instructions, which when executed by the processing device, causes the processing device to perform one or more of the functions, methods, or operations, described herein. For example, computing device 801 includes pupil edge region removal module 198. Pupil edge region removal module 198 is configured to perform the functions and operations described herein. An example computing device 801 is illustrated and discussed in more detail with reference to FIG. 12.

Figure 4:
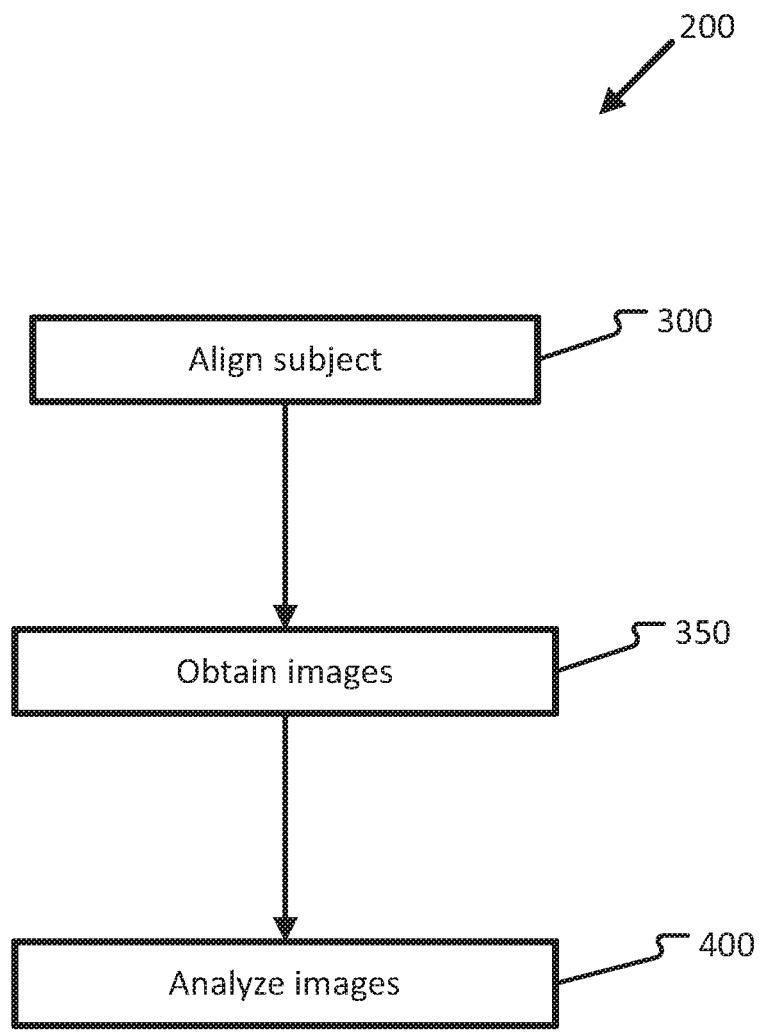
FIG. 4 shows an example method of imaging/screening a subject using the example medical imaging environment of FIG. 2.

FIG. 4 illustrates example method 200 for imaging/screening a subject. Example method 200 includes aligning a subject (operation 300), obtaining digital images (operation 350), and analyzing the digital images (operation 400). Example method 200 is typically performed using medical digital imaging system 102 described above. Example method 200 can be performed without administering mydriatic substances to the subject and, accordingly, a subject's pupil dilation is usually no greater than 5 mm. Other embodiments can include more or fewer operations.

Example method 200 begins by aligning a subject (operation 300). Aligning a subject (operation 300) can include adjusting a relative spacing between the subject and the medical digital imaging system. In some implementations, the subject is seated in a chair during examination. Alternatively, the subject may be aligned using one or more features on the medical digital imaging system, such as a chin rest. In some instances, a user holds a hand-held version of medical digital imaging system and can move closer or further away from the subject while the subject is sitting or standing. Alignment of the subject and medical digital imaging system can be guided by on-screen displays that can instruct the user to move in one or more directions. Range finding units can guide this alignment.

After aligning the subject (operation 300), one or more digital images are obtained (operation 350). During imaging (operation 350), the medical digital imaging system displays one or more visual stimuli to the subject. Digital images captured during operation 350 are typically images of the subject's pupil or ocular fundus.

After one or more digital images are obtained (operation 350), the images are analyzed (operation 400). Analyzing the images (operation 400) varies depending upon the purpose for the subject's examination. For instance, in refractive error screening implementations, image analysis (operation 400) includes processing one or more digital images to determine whether the subject has refractive error. Based on image analysis (operation 400), one or more results can be displayed to the user.

Figure 5:
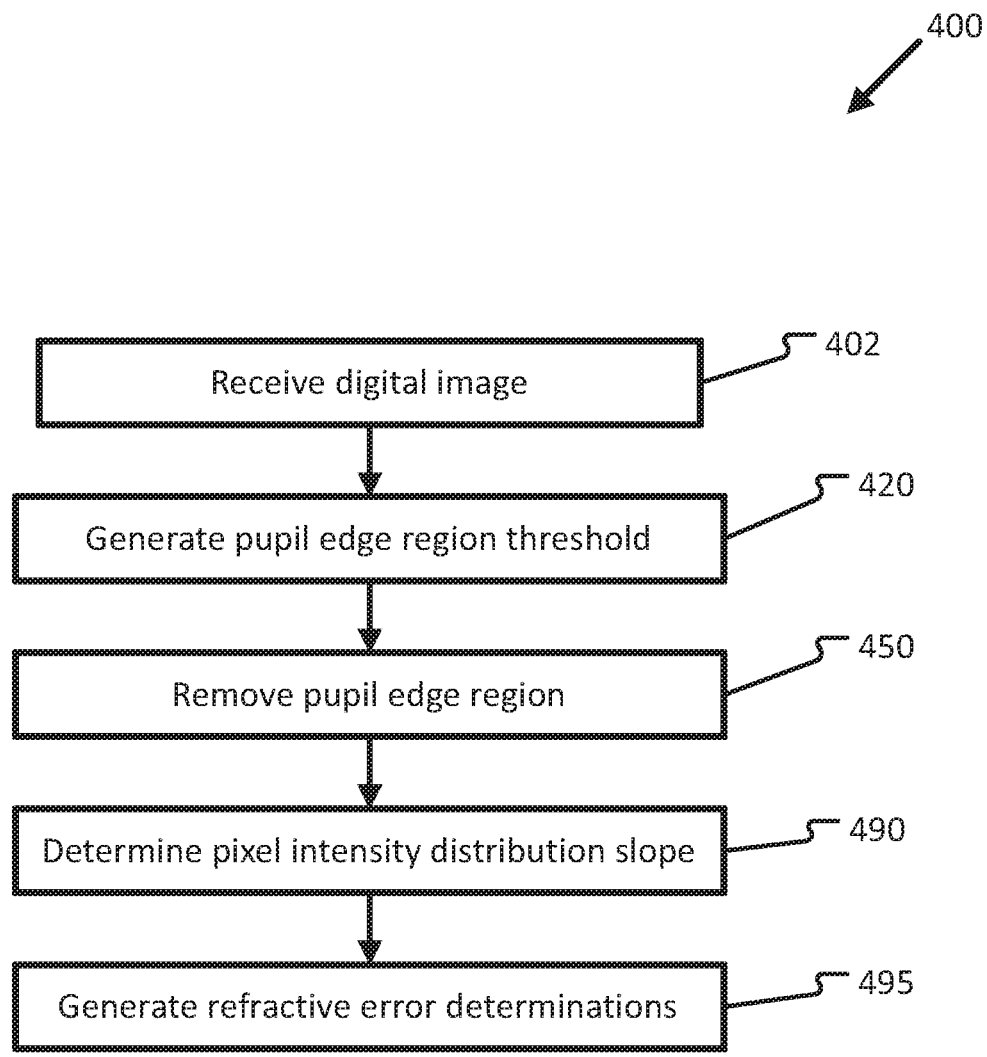
FIG. 5 shows example operations performed during the image analysis operation of FIG. 4.

FIG. 5 illustrates example operations performed during image analysis (operation 400). As shown, image analysis (operation 400) includes receiving a digital image (operation 402), generating a pupil edge region threshold (operation 420), removing a pupil edge region (operation 450), determining pixel intensity distribution slope (operation 490), and generating refractive error determinations (operation 495). Other embodiments can include more or fewer operations.

Image analysis (operation 400) typically begins by receiving a digital image (operation 402). Digital images received during operation 402 are captured by the image sensor array in the medical digital imaging system. These images are usually captured during near-infrared illumination or visible light illumination. In some instances, one or more digital images are received from an external apparatus or retrieved from remote storage.

In some implementations, the digital image received (operation 402) has been processed to include a pupil candidate region. Generally, the pupil candidate region is a portion of a captured digital image that includes the pupil of a test subject. Determining a pupil candidate region is described in detail in U.S. Pat. No. 9,402,538.

The pupil candidate region is square or rectangular shaped. Typically, the pupil candidate region is square and has side lengths between 70 and 80 pixels. The pupil candidate region is usually larger than 65 pixels by 65 pixels to provide additional space between the pupil edges and the edge areas of the pupil candidate region. In some implementations, the pupil candidate region is 11.5 mm by 11.5 mm. In other implementations, the pupil candidate region is 71 pixels by 71 pixels. Other sizes of pupil candidate region are contemplated.

After receiving one or more digital images (operation 402), a pupil edge region threshold is determined (operation 420). Broadly, determining a pupil edge region threshold (operation 420) includes operations resulting in generation of a threshold that can be used to remove the pupil edge region pixels. Additional details regarding determining a pupil edge region threshold (operation 420) are described below with reference to, at least, FIG. 6.

After determining a pupil edge region threshold (operation 420), the pupil edge region is removed (operation 450). Generally, removing the pupil edge region (operation 450) includes identifying a plurality of pixels in the digital pupil image that are at, and near, the pupil edge and generating resulting data, typically an image, without those pupil edge region pixels. Additional details regarding removing the pupil edge region (operation 450) are described below with reference to, at least, FIG. 7.

Using the data resulting from removing the pupil edge region (operation 450), a pixel intensity distribution slope is determined (operation 490). Example determinations of a slope of the pixel intensity distribution across a pupil are shown and described in U.S. Pat. No. 9,237,846, titled "Photorefraction ocular screening device and methods," with particular reference to FIG. 15. For example, determining intensity distribution slope can include identifying a portion of the pupil area and generating a profile vector having 25 pixel elements.

Using the pixel intensity distribution slope, a refractive error determination is generated (operation 495).). Example determinations of refractive error are shown and described in U.S. Pat. No. 9,237,846, titled "Photorefraction ocular screening device and methods."

Figure 6:
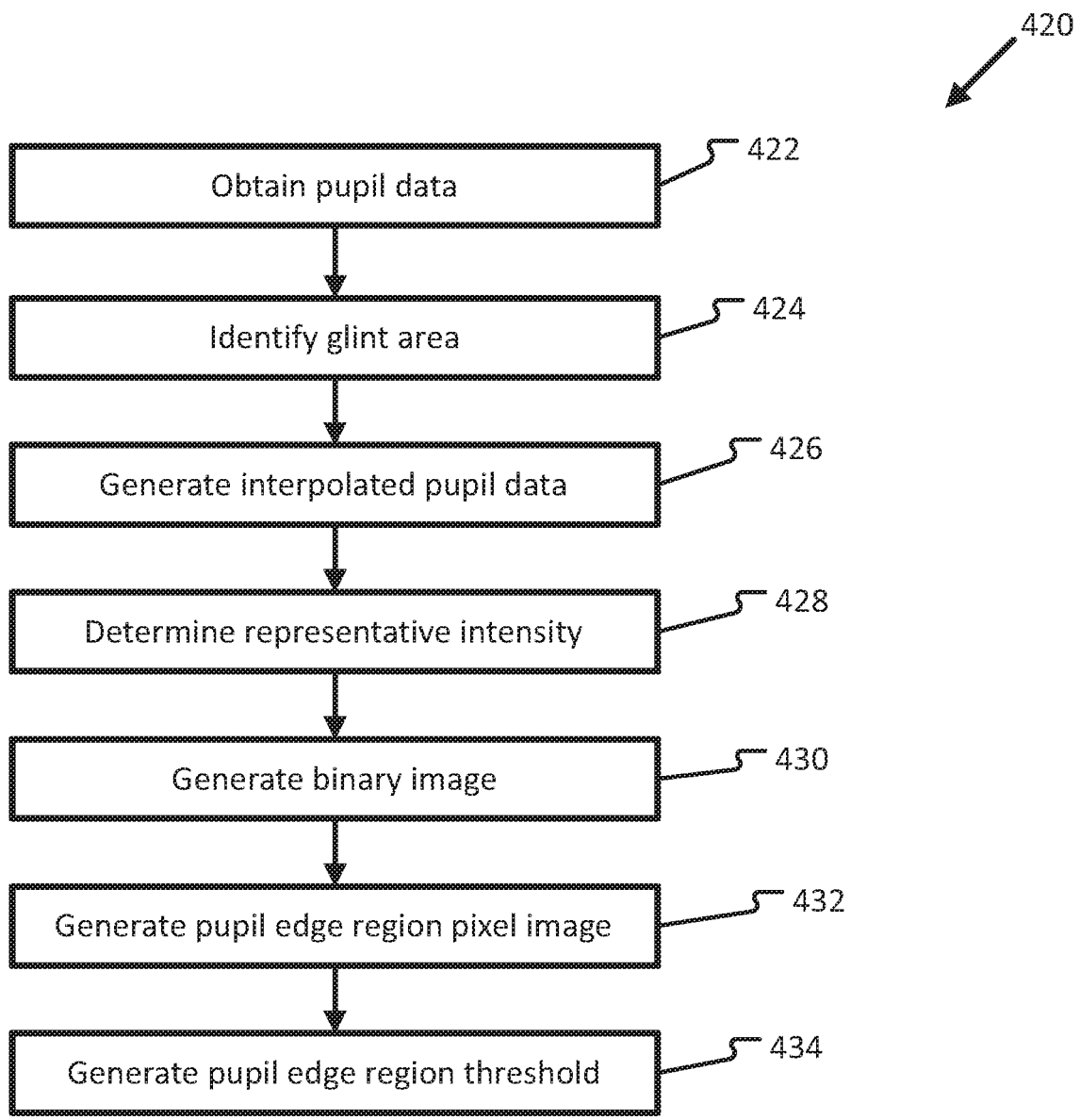
FIG. 6 shows example operations performed during the pupil edge region threshold determination operation of FIG. 5.

FIG. 6 shows additional details of determining a pupil edge region threshold (operation 420). Typically, determining a pupil edge region threshold (operation 420) includes obtaining pupil data (operation 422), identifying a glint area (operation 424), generating interpolated pupil data (operation 426), determining a representative intensity (operation 428), generating a binary image (operation 430), generating a pupil edge region pixel image (operation 432), and generating a pupil edge region threshold (operation 434).

After receiving the digital image (operation 402), pupil data are obtained (operation 422). Pupil data include attributes of the pupil in the digital image. For example, pupil data can include coordinates of a center point of the pupil, a radius of the pupil, and pixels that are likely part of the pupil. Example processes for determining various pupil data are described in in U.S. Pat. No. 9,237,846, titled "Photorefraction ocular screening device and methods" and U.S. patent application Ser. No. 15/926,121, "Pupil Edge Detection in Digital Imaging," filed on even date herewith.

At some point after receiving the digital image (operation 402), a glint area of the digital image is identified (operation 424). The glint area includes pixels that are part of the subject's glint. The subject's glint is a bright specular reflection of the near-infrared LED(s) from the outer surface of the cornea. Example processes for determining a glint area are described in in U.S. Pat. No. 9,237,846, titled "Photorefraction ocular screening device and methods."

Next, interpolated pupil data are generated (operation 426). Broadly, interpolated pupil data are replacement values or pixels for those pixels that are in the glint area. The interpolated pupil data are generated, broadly speaking, by identifying intensity values for neighboring pupil pixels that are not part of the glint area and determining a value consistent with those neighboring intensities. Then these values replace the glint area pixels in a modified image or data set.

Relative to pupil sizes less than 5 mm, larger pupil sizes have lots of pixels that can be used for determining an intensity distribution. Removing glint area pixels in the larger pupil size images still leaves enough pupil pixels to accurately generate a threshold value for identifying pupil edge region pixels.

Generating interpolated pupil data is particularly valuable for pupil sizes below a threshold, such as less than 5 mm. In smaller pupil sizes, typically less than 5 mm, without generating interpolated pupil data, removing the glint area pixels and determining an intensity distribution on the remaining pupil pixels results in sample sizes that are too small. That is, typically there are not enough remaining pupil pixels to generate an accurate threshold value that can be used to identify pupil edge region pixels.

After generating interpolated pupil data (operation 426), a representative intensity is determined (operation 428). The representative intensity is a value representing intensity values of pupil pixels, as compared to pupil edge region pixels or iris pixels. The representative intensity can be used as a threshold value when binarizing the image (operation 430).

As noted above, pupil data obtained during operation 422 can be used to identify those pixels that are part of the pupil. Determining a representative intensity (operation 428) can include generating intensity values for each pixel within the pupil. In some instances, intensity values for each pupil pixel have already been determined.

In some implementations, determining a representative intensity (operation 428) includes calculating a mean of the pupil pixel intensity values. That is, the intensity value for each pixel is summed and divided by the number of pixels summed. Then the mean pupil pixel intensity can be multiplied by a multiplier, resulting in the representative intensity (or threshold). Typically, the multiplier is greater than 1 and less than 3. In some implementations, the multiplier is 2.

Other methods of determining a representative intensity (operation 428) are possible. For example, a mean intensity of the interpolated pixels is determined and, separately, a mean intensity of the non-interpolated pixels (the non-glint pixels) is determined. Then, the representative intensity is determined by weighting the non-interpolated pixel mean higher than the interpolated pixel mean. A resulting mean can be multiplied by the multiplier described above.

After determining a representative intensity (operation 428), a binary image is generated (operation 430). Broadly, generating a binary image (operation 430) involves converting the digital pupil image into an image or grid where each pixel has one of two values, typically a 0 or a 1. The resulting image or grid is a representation of the pupil in the digital pupil image.

Typically, the digital pupil image pixels have one or more values. For example, if the digital pupil image is in black and white, each pixel has one value, typically on a scale of 0-255. In some instances, this value can be the same as a pixel intensity value. If the digital pupil image in color, each pixel can have three values (one red value, one green value, and one blue value), where each value is typically on a scale of 0-255. In some implementations, an intensity value has been determined for each pixel.

Generating a binary image (operation 430) includes evaluating a value, such as the pixel intensity value, of each pixel in the digital image against the threshold value (the representative intensity). If a pixel value is less than the threshold value, then that pixel is assigned a value corresponding to pixel intensities below the threshold, such as 0. If the pixel value is greater than the threshold value, then that pixel is assigned a value corresponding to pixel intensities above the threshold, such as 1.

Using the generated binary image (operation 430), a pupil edge region pixel image is generated (operation 432). Generating a pupil edge region pixel image (operation 432) results in an image or data array where the pupil edge region pixels are prominent. Alternatively, the resulting image or data array from operation 432 has the pupil edge region pixels as the only non-zero intensity value pixels.

In some implementations, generating a pupil edge region pixel image (operation 432) can include mapping the binary image to the received digital image. Any pixels that were identified as being part of the pupil (from operation 422) and that have a non-zero value in the binary image, are removed as being part of the central pupil. The pixels that were identified as being part of the pupil but given a zero value in the binary image are the pupil edge region pixels, and those remain in the pupil edge region pixel image. As mentioned above, "removed" can include assigning a pixel intensity that is similar to the iris and not actually removing the pixels from the digital image.

Using the pupil edge region pixel image (operation 432), a pupil edge region threshold value is generated (operation 434). Generally, the pupil edge region threshold value represents the intensity values of the pupil edge region pixels. Generating the pupil edge region threshold value (operation 434) typically includes calculating a mean of each pupil edge region pixel intensity value. In some instances, that mean can be multiplied by a multiplier. The resulting pupil edge region threshold value is used during removing the pupil edge region (operation 450).

Figure 7:
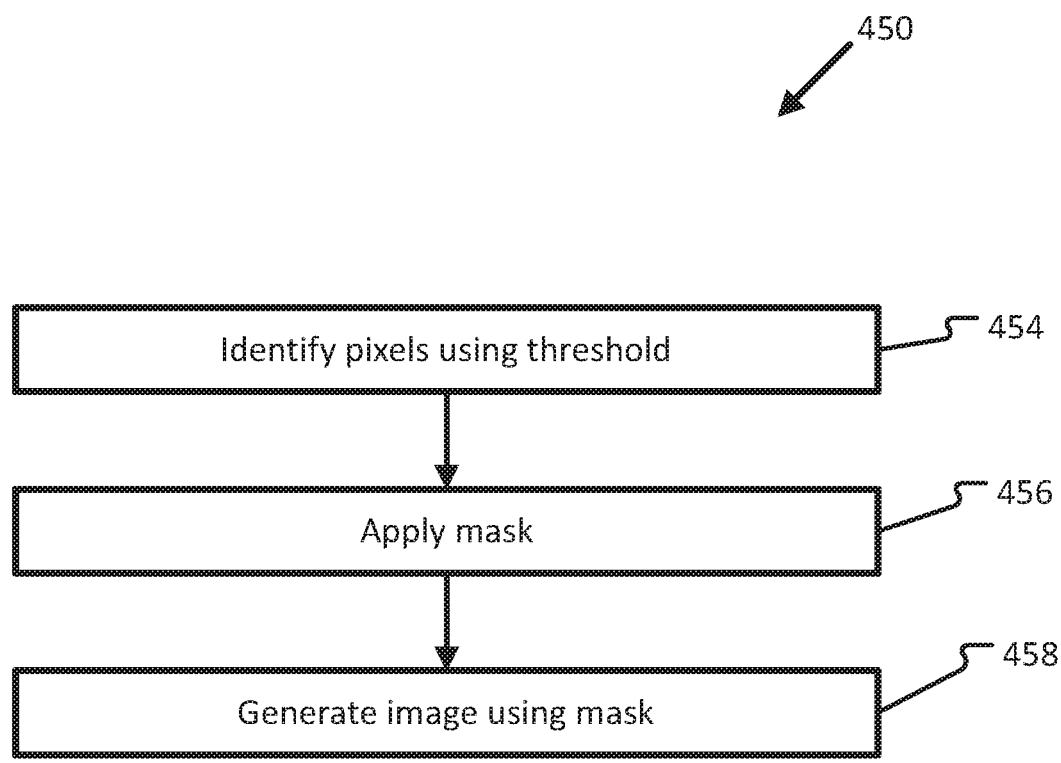
FIG. 7 shows example operations performed during the removing a pupil edge region operation of FIG. 5.

FIG. 7 shows additional details of removing a pupil edge region (operation 450). Typically, removing a pupil edge region (operation 450) includes identifying pixels using the pupil edge region threshold (operation 454), applying a mask (operation 456), and generating an image using the mask (operation 458).

After generating the pupil edge region threshold (operation 434 in FIG. 6), pupil edge region pixels are identified using the pupil edge region threshold. Then, a mask is applied (operation 456) to those identified pupil edge region pixels in the original digital image from operation 402. Broadly, the mask is an identification of pixels to be removed from the original image. By applying the mask, a new image is generated (operation 458) that can be used for subsequent processing. The image generated in operation 458 does not include the pupil edge region pixels.

Example

Figure 8:
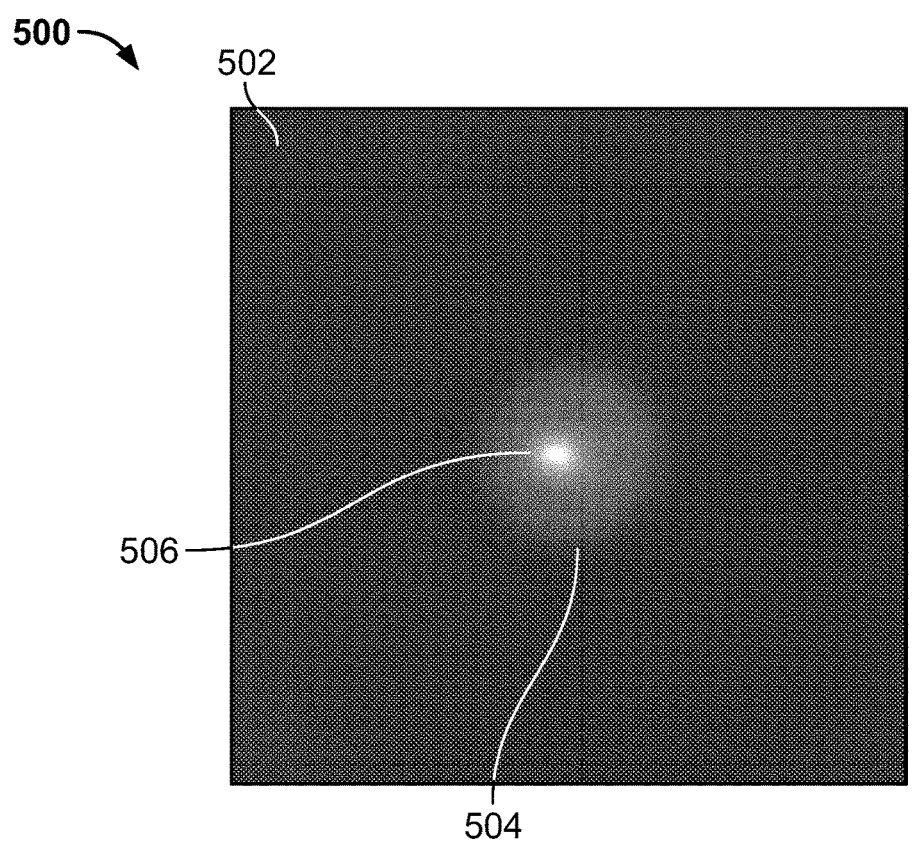
FIG. 8 shows an example digital pupil image.

FIGS. 8-11 show exemplary image data generated during image analysis method 400 described above. FIG. 8 shows digital pupil image 500 received during operation 402. Digital pupil image 500 includes iris area 502, pupil 504, and glint 506. Pupil 504 is a 3 mm pupil. Previous processing has determined that digital pupil image 500 likely includes the subject's pupil.

Figure 9:
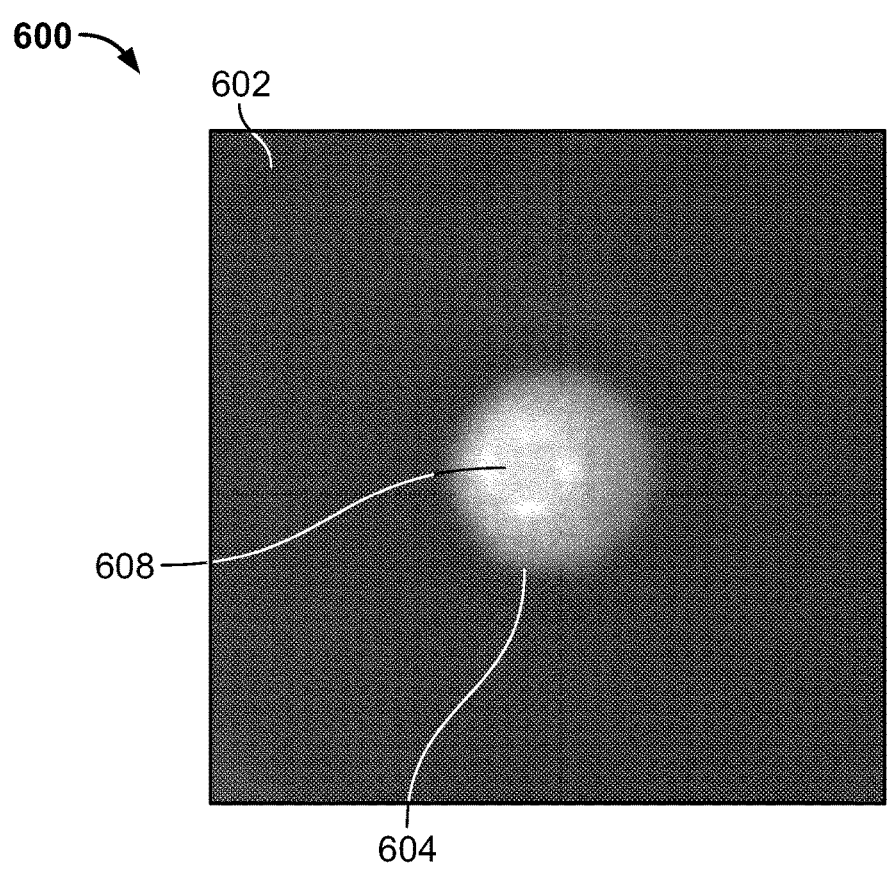
FIG. 9 shows an example digital pupil image after interpolating a glint area.

FIG. 9 shows digital pupil image 600 after interpolating a glint area. An exemplary embodiment of interpolating a glint area is shown in FIG. 6 as operation 426. Digital pupil image 600 includes iris area 602, pupil 604 and interpolated glint area 608. Comparing pupil 604 with pupil 504 in FIG. 8, it is seen that the pixel intensity is more consistent across pupil 604 than pupil 504 because the glint area 504 has been removed.

Figure 10:
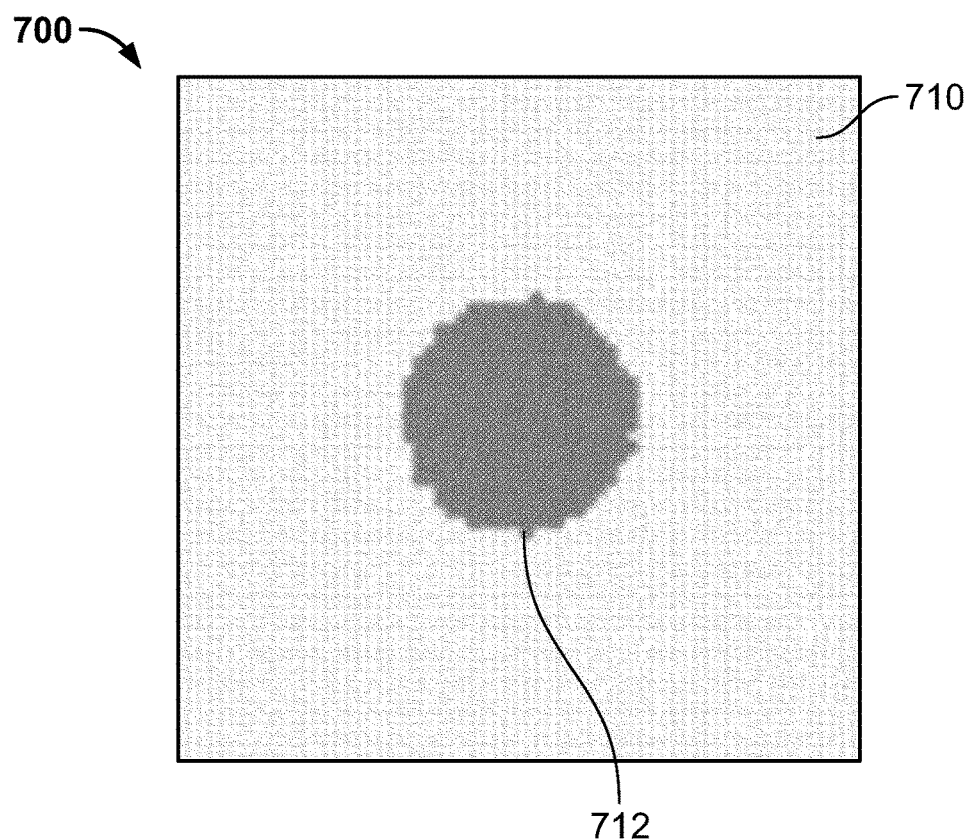
FIG. 10 shows an example binarized image.

FIG. 10 shows binarized image 700 generated using a threshold. An exemplary embodiment of generating a threshold and generating a binary image are shown in FIG. 6 as operations 428 and 430, respectively. Binarized image 700 includes non-zero pupil portion 712 and non-pupil area 710. Each pixel in binarized image 700 is assigned one of two values, such as a 0 or a 1.

Figure 11:
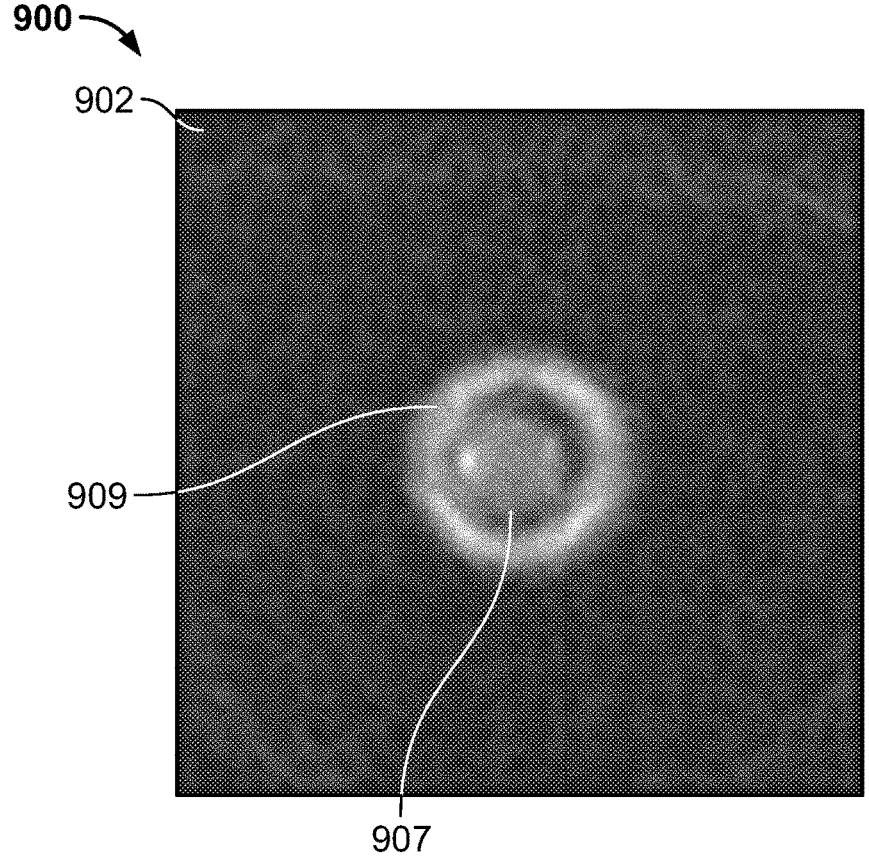
FIG. 11 shows an example digital pupil edge image.

FIG. 11 shows digital pupil edge image 900. Digital pupil edge image 900 includes iris area 902, removed center pupil area 907, and pupil edge region 909. Digital pupil edge image 900 was generated by applying binarized image 700 to digital pupil image 600. An exemplary embodiment of generating digital pupil edge image 900 is shown in FIG. 6 as operation 432.

Figure 12:
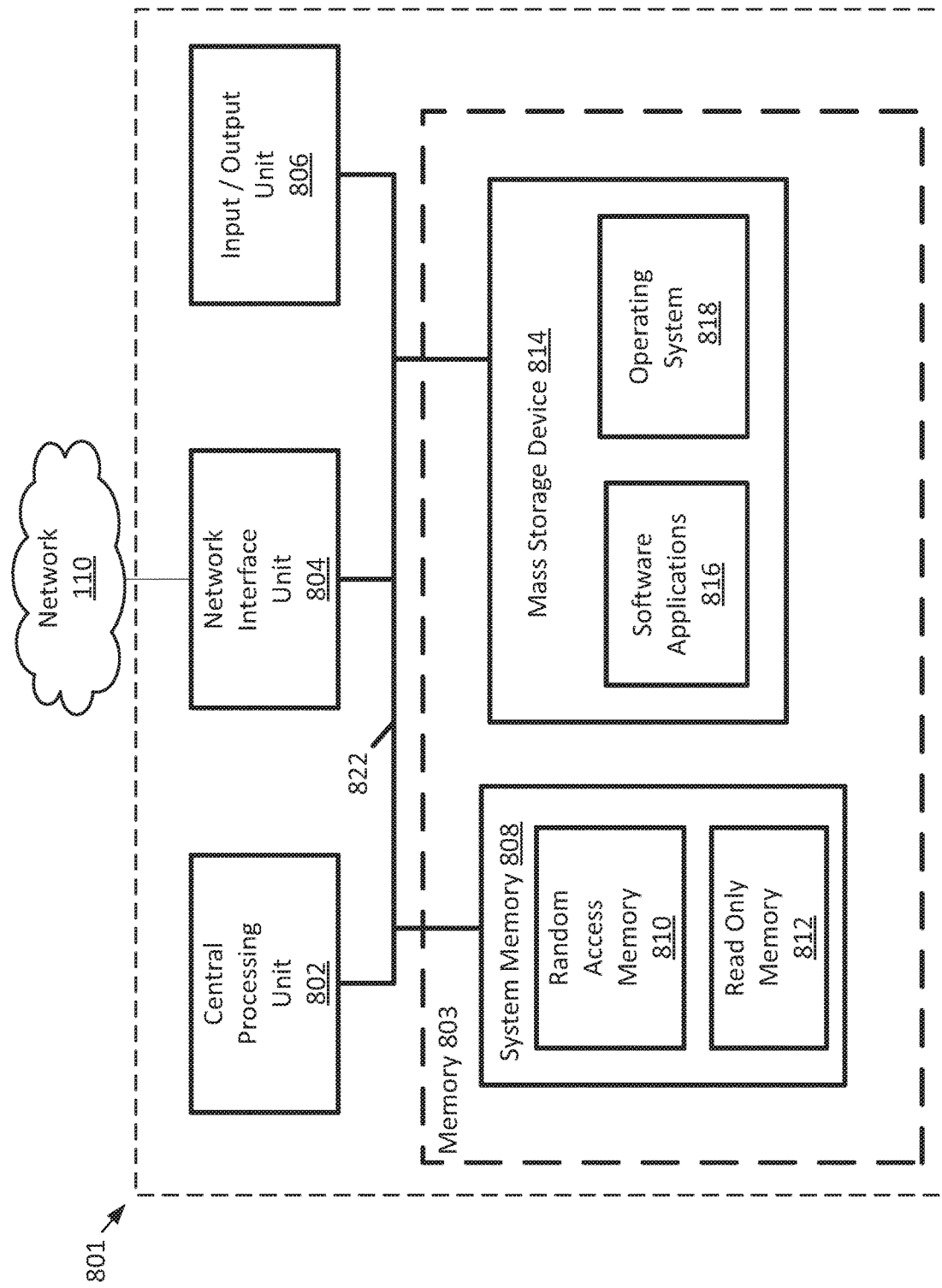
FIG. 12 shows example physical components of a computing device of the medical digital imaging system shown in FIG. 3.

FIG. 12 shows an example computing device 801 of medical digital imaging system 102. As illustrated, example computing device 801 includes at least one central processing unit ("CPU") 802, memory 803, and a system bus 822 that couples memory 803 to the CPU 802. Memory 803 includes system memory 808 and mass storage device 814. System memory 808 includes a random access memory ("RAM") 810 and a read-only memory ("ROM") 812. A basic input/output system that contains the basic routines that help to transfer information between elements within the example computing device 801, such as during startup, is stored in the ROM 812. Memory 803 further includes mass storage device 814. Mass storage device 814 is able to store software applications 816, operating system 818, and data.

Mass storage device 814 is connected to CPU 802 through a mass storage controller (not shown) connected to the system bus 822. Mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central processing unit can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments, the example computing device 801 may operate in a networked environment using logical connections to remote network devices through the network 110, such as a wireless network, the Internet, or another type of network. The example computing device 801 may connect to the network 110 through a network interface unit 804 connected to the system bus 822. The network 110 may be a protected network. It should be appreciated that the network interface unit 804 may also be utilized to connect to other types of networks and remote computing systems. The example computing device 801 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing device 801 can store software instructions and data. The software instructions include an operating system 818 suitable for controlling the operation of the example computing device 801. The mass storage device 814 and/or the RAM 810 also store software applications 816, that when executed by the CPU 802, cause the example computing device 801 to provide the functionality of the example computing device 801 discussed in this disclosure. For example, the mass storage device 814 and/or the RAM 810 can store software instructions that, when executed by the CPU 802, cause the medical digital imaging system 102 to remove pupil edge region pixels in digital images.

Although various embodiments are described herein, those of ordinary skill in the art will understand that many modifications may be made thereto within the scope of the present disclosure. Accordingly, it is not intended that the scope of the disclosure in any way be limited by the examples provided.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A method for removing a pupil edge region from a digital image, the method comprising:
   identifying a plurality of pupil pixels in the digital image;
   identifying a glint area in the plurality of pupil pixels;
   generating interpolated pupil data, including interpolating a first portion of the plurality of pupil pixels, the first portion including the glint area;
   determining a representative intensity of the interpolated pupil data;
   using the representative intensity, generating a threshold;
   generating a binary image of the digital image using the threshold;
   removing a pupil area of the binary image;
   averaging remaining outer pupil pixel intensity values in the binary image, thereby generating a pupil edge region threshold; and
   removing the pupil edge region from the digital image using the pupil edge region threshold;
   wherein removing the pupil edge region includes removing pixels having an intensity value that is lower than the pupil edge region threshold.

2. The method according to claim 1, wherein removing the pupil edge region from the digital image includes applying a mask to the digital image.

3. The method according to claim 2, wherein removing the pupil edge region from the digital image includes removing pixels included in the mask.

4. The method according to claim 1, wherein interpolating the first portion of the plurality of pupil pixels includes identifying probable glint pixels, the probable glint pixels being likely to be part of the glint area.

5. The method according to claim 4, wherein interpolating the first portion of the plurality of pupil pixels includes:
   generating new pixel values for the probable glint pixels, including evaluating intensity values for pixels proximate to the probable glint pixels; and
   replacing the probable glint pixels with the new pixel values.

6. The method according to claim 5, wherein determining the plurality of pupil pixels includes:
   obtaining a center point of a pupil in the digital image; and
   obtaining a radius of the pupil in the digital image.

7. The method according to claim 6, the radius of the pupil being no greater than 2.5 mm.

8. The method according to claim 1, wherein the representative intensity is a mean of the interpolated pupil data.

9. The method according to claim 1, wherein generating the threshold includes multiplying the representative intensity by a multiplier; and
   wherein removing the pupil area of the binary image includes removing a center area of a pupil.

10. The method according to claim 9, wherein the multiplier is greater than 1 and no greater than 3.

11. The method according to claim 10, wherein the multiplier is 2.

12. A method for generating a mask of a pupil edge region in a digital image, the method comprising:
   receiving the digital image;
   identifying a plurality of pupil pixels in the digital image;
   identifying a glint area in the plurality of pupil pixels;
   generating interpolated pupil data, including interpolating a first portion of the plurality of pupil pixels, the first portion including the glint area, wherein interpolating the first portion of the plurality of pupil pixels includes:
      identifying probable glint pixels, the probable glint pixels being likely to be part of the glint area;
      generating new pixel values for the probable glint pixels, including evaluating intensity values for pixels proximate to the probable glint pixels; and
      replacing the probable glint pixels with the new pixel values;
   determining a representative intensity of the interpolated pupil data;
   using the representative intensity, generating a threshold;
   generating a binary image of the digital image using the threshold;
   removing a center pupil area of the binary image;
   averaging remaining outer pupil pixel intensity values in the binary image, thereby generating a pupil edge region threshold;
   using the pupil edge region threshold, applying the mask to the digital image; and
   removing pixels included in the mask from the digital image.

13. The method according to claim 12, wherein determining the plurality of pupil pixels includes:
   obtaining a center point of a pupil in the digital image; and
   obtaining a radius of the pupil in the digital image.

14. The method according to claim 13, wherein the representative intensity is a mean of the interpolated pupil data; and
   wherein generating the threshold includes multiplying the representative intensity by a multiplier, the multiplier being greater than 1 and no greater than 3.

15. A medical imaging system, comprising:
   an illumination assembly;
   a digital camera assembly;
   a processing unit; and
   memory storing instructions that, when executed by the processing unit, cause the medical imaging system to:
      illuminate an eye fundus of a subject with the illumination assembly;
      receive a digital image with the digital camera assembly;
      identify a plurality of pupil pixels in the digital image;
      identify a glint area in the plurality of pupil pixels;
      generate interpolated pupil data, including interpolating a first portion of the plurality of pupil pixels, the first portion including the glint area, wherein interpolating the first portion of the plurality of pupil pixels includes to:
         identify probable glint pixels, the probable glint pixels being likely to be part of the glint area;
         generate new pixel values for the probable glint pixels, including evaluating intensity values for pixels proximate to the probable glint pixels; and
         replace the probable glint pixels with the new pixel values;
      determine a representative intensity of the interpolated pupil data;
      use the representative intensity to generate a threshold;

generate a binary image of the digital image using the threshold;

remove a center pupil area of the binary image;

average remaining outer pupil pixel intensity values in the binary image, thereby generating a pupil edge region threshold; and remove a pupil edge region from the digital image using the pupil edge region threshold, including removing pixels having an intensity value that is lower than the pupil edge region threshold.

16. The medical imaging system according to claim 15, wherein the representative intensity is a mean of the interpolated pupil data;

wherein generating the threshold includes to multiply the representative intensity by a multiplier, the multiplier being greater than 1 and no greater than 3; and wherein determining the plurality of pupil pixels includes to:

obtain a center point of a pupil in the digital image; and obtain a radius of the pupil in the digital image.

* * * * *